(12) United States Patent
Corma et al.

(10) Patent No.: US 9,120,090 B2
(45) Date of Patent: Sep. 1, 2015

(54) MODIFIED ZEOLITE CATALYST

(75) Inventors: Avelino Corma, Valencia (ES); Cristina Martinez, Valencia (ES); Eric J. Doskocil, Oswego, IL (US); George Yaluris, Park Ridge, IL (US)

(73) Assignees: BP Oil International Limited, Sunbury on Thames (GB); BP Corporation North America Inc., Houston, TX (US)

( * ) Notice: Subject to any disclaimer, the term of this patent is extended or adjusted under 35 U.S.C. 154(b) by 312 days.

(21) Appl. No.: 13/377,725

(22) PCT Filed: Jun. 22, 2010

(86) PCT No.: PCT/US2010/039407
§ 371 (c)(1),
(2), (4) Date: Mar. 28, 2012

(87) PCT Pub. No.: WO2011/002630
PCT Pub. Date: Jan. 6, 2011

(65) Prior Publication Data
US 2012/0178615 A1 Jul. 12, 2012

(30) Foreign Application Priority Data
Jul. 3, 2009 (EP) ..................................... 09380129

(51) Int. Cl.
| | |
|---|---|
| B01J 29/06 | (2006.01) |
| B01J 35/10 | (2006.01) |
| B01J 29/44 | (2006.01) |
| B01J 29/70 | (2006.01) |
| B01J 29/72 | (2006.01) |
| B01J 29/78 | (2006.01) |
| B01J 37/06 | (2006.01) |
| C01B 39/02 | (2006.01) |
| C07C 1/20 | (2006.01) |
| C10G 50/00 | (2006.01) |

(52) U.S. Cl.
CPC .............. *B01J 35/1038* (2013.01); *B01J 29/44* (2013.01); *B01J 29/7042* (2013.01); *B01J 29/7092* (2013.01); *B01J 29/7284* (2013.01); *B01J 29/7884* (2013.01); *B01J 35/1061* (2013.01); *B01J 37/06* (2013.01); *C01B 39/026* (2013.01); *C07C 1/20* (2013.01); *C10G 50/00* (2013.01); *B01J 35/109* (2013.01); *B01J 2229/16* (2013.01); *B01J 2229/22* (2013.01); *B01J 2229/32* (2013.01); *B01J 2229/37* (2013.01); *B01J 2229/38* (2013.01); *C07C 2521/04* (2013.01); *C07C 2521/08* (2013.01); *C07C 2521/12* (2013.01); *C07C 2529/70* (2013.01); *C07C 2529/76* (2013.01); *C07C 2529/78* (2013.01); *C10G 2300/70* (2013.01)

(58) Field of Classification Search
USPC ........ 502/60, 63, 64, 65, 66, 73, 74; 423/700, 423/714, 716
See application file for complete search history.

(56) References Cited

U.S. PATENT DOCUMENTS

| | | | | |
|---|---|---|---|---|
| 4,902,406 | A | * | 2/1990 | Valyocsik ..................... 208/118 |
| 5,118,482 | A | | 6/1992 | Narayana et al. |
| 5,248,841 | A | | 9/1993 | Young |
| 6,124,227 | A | | 9/2000 | Yao et al. |
| 6,583,186 | B2 | * | 6/2003 | Moore, Jr. ...................... 518/700 |
| 6,620,402 | B2 | * | 9/2003 | Jacobsen et al. ............... 423/716 |
| 6,793,911 | B2 | * | 9/2004 | Koegler et al. ................ 423/716 |
| 6,998,104 | B2 | * | 2/2006 | Tao et al. ....................... 423/716 |
| 7,410,924 | B2 | | 8/2008 | Corma Canos et al. |
| 2005/0239634 | A1 | * | 10/2005 | Ying et al. ....................... 502/64 |
| 2007/0227351 | A1 | * | 10/2007 | Garcia-Martinez ............... 95/90 |

FOREIGN PATENT DOCUMENTS

WO  WO 2008/147190  12/2008

OTHER PUBLICATIONS

Tao et al., "Mesopore-Modified Zeolites: Preparation, Characterization, and Applications", Chem. Rev. 106, 2006, pp. 896-910.*
Groen et al., "On the introduction of intracrystalline mesoporosity in zeolites upon desilication in alkaline medium", Microporous and Mesoporous Materials, 69, 2004, pp. 29-34.*
Ogura et al., "Formation of Uniform Mesopores in ZSM-5 Zeolite through Treatment in Alkaline Solution", Chemistry Letters, 2000, pp. 882-883.*
Corma et al., "Zeolites in refining and petrochemistry", Studies in Surface Science and Catalysis, 157, 2005, pp. 337-366.*
Verboekend et al., "Mesoporous ZSM-22 zeolite obtained by desilication: peculiarities associated with crystal morphology and aluminum distribution", CrystEngComm 13, 2011, pp. 3408-3416.*
Qiang et al., Characterization and Catalytic Performance of Alkali-Treated Mordenite for Synthesis of Ethyl Tertiary Butyl Ether, Chinese Journal of Catalysis, vol. 26, No. 3, Mar. 2005, pp. 243-247.

(Continued)

*Primary Examiner* — Elizabeth Wood
(74) *Attorney, Agent, or Firm* — Kelly L. Cummings; Ekkehard Schoettle

(57) ABSTRACT

A modified zeolite catalyst derived from a zeolite of a structural type which consists of a one-dimensional micropore structure of channels made from rings containing between 8 and 12 silicon/aluminum atoms is disclosed. It consists substantially of a plurality of crystallites having additional mesoporosity whose volume is in the range 0.09 to 0.25 cc/g as mentioned by nitrogen adsorption at 77° K and calculated by the BJH method. The mesoporosity may be introduced into the crystallites by e.g. treatment with aqueous sodium hydroxide at a pH at 25° C. in excess of 8 for an extended period at elevated temperature. The catalyst shows improved resistance to catalyst deactivation and greater selectivity to higher hydrocarbons when used to e.g. oligomerize light alkenes e.g. propene or the butenes.

12 Claims, 4 Drawing Sheets

(56) References Cited

OTHER PUBLICATIONS

Figure 1:
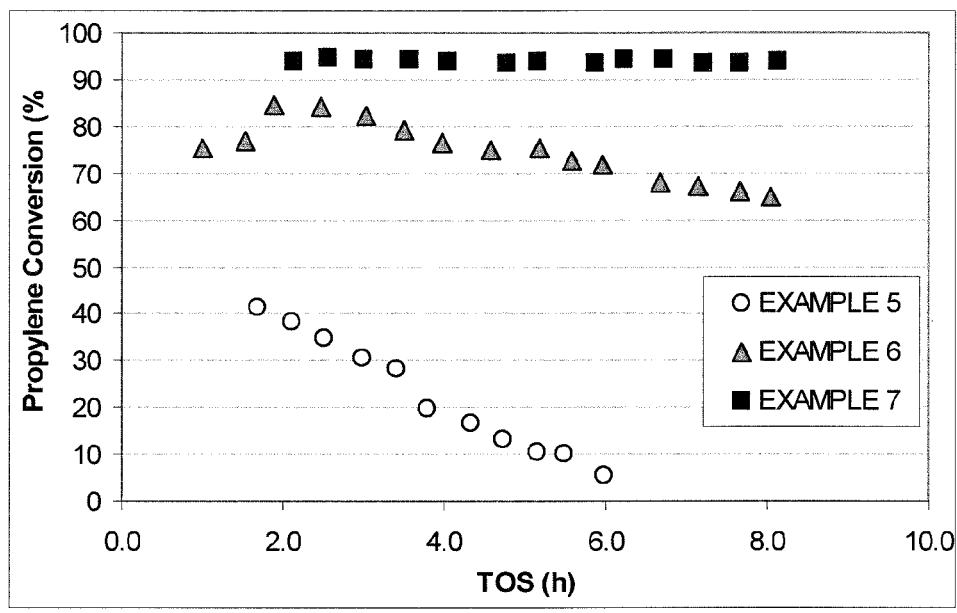

Barrett et al., The Determination of Pore Volume and Area Distributions in Porous Substances. I. Computations from Nitrogen Isotherms., [Contribution from the Multiple Fellowship of Baugh and Sons Company, Mellon Institute], Jan. 1951, pp. 373-380.

Organisation Intergouvernmentale de la Convention du Mètre, The Interntaional System of Units (SI), 8th Edition, 2006, cover page, pp. 113-114.

Derewinksi et al., Thermal Stability and Siting of Aluminum in Isostructural ZSM-22 and Theta-1 Zeolites, Catalysis Today, 114 (2006), pp. 197-204.

International Search Report corresponding to PCT Patent Application No. PCT/US2010/039407, dated Jan. 20, 2011.

* cited by examiner

Naphtha: C5-446.9 K
Diesel: 446.9-664.1 K
Heavy fraction: 664.1-1273 K

Naphtha: C5-446.9 K
Diesel: 446.9-664.1 K
Heavy fraction: 664.1-1273 K

MODIFIED ZEOLITE CATALYST

The present invention relates to a modified zeolite catalyst having a one-dimensional micropore structure consisting of channels made from rings containing between 8 and 12 silicon/aluminium atoms, especially those of the 10-ring TON structural type, which are suitable for use inter alia as a catalyst for oligomerizing lower hydrocarbons and alcohols to produce a higher hydrocarbon fraction suitable for use as gasoline or diesel fuel.

The oligomerization of light alkenes, such as propene and the butenes, represents an important industrial route to the production of environmentally friendly synthetic liquid fuels, free of sulphur and aromatics. These processes allow the production of hydrocarbon mixtures in the boiling range of gasoline or diesel depending on the exact nature of the catalyst and its operating conditions. For example it is known that high temperatures (>300° C.) and low pressures (<30 bar) will increase the gasoline yield, whereas lower temperatures and higher pressures will favour the formation of heavier oligomers in the diesel fraction.

Zeolites having a one-dimensional micropore structure consisting of channels made from rings containing between 8 and 12 silicon/aluminium atoms, for example ZSM 12 and zeolites of the TON structural type such as Theta-1 and ZSM-22, are known and in the past have been proposed as catalysts for hydrocarbon processing. However a combination of their needle-like crystallite morphology and one-dimensional micropore structure makes them especially prone to deactivation by coking mechanisms which block the entrances to the internal micropore structure. A number of approaches for overcoming this have been disclosed in the art; for example, U.S. Pat. No. 5,284,989 discloses inter alia, treating ZSM-22, with a dicarboxylic acid to inactivate potential coking sites on the exterior of the crystallite. Several patents (WO95/19945; WO95/22516; U.S. Pat. No. 6,143,942) claim the use of ZSM-22 either alone or in admixture with other zeolites, to oligomerize light olefins. In this way they are able to control the oligomerization degree of the olefins.

FR2887538A1 describes the use of a range of different zeolites, including those of the TON structural type, which have been first dealuminated in a first step followed by treatment with a silicon compound and finally converted to the hydrogen form. FR2894850A1 describes the use of modified TON zeolites as catalysts in an oligomerization process to obtain diesel or jet fuel. The catalysts are prepared by impregnating the zeolite with Group VIB and VIII metals followed by gas phase deposition of amorphous $SiO_2$. The final catalysts are used in their acid form.

It has now been found that zeolites having a one-dimensional micropore structure which have been treated with an alkaline solution exhibit improved resistance to catalyst deactivation when used in hydrocarbon and alcohol conversion processes. Moreover electron microscopy of the treated samples reveal that the effect of this treatment has been to introduce mesoporosity into the crystallites thereby providing greater access to the interior of the crystallites.

According to the present invention there is therefore provided a modified zeolite catalyst derived from a zeolite of a structural type which consists of a one-dimensional micropore structure of channels made from rings containing between 8 and 12 silicon/aluminium atoms characterised in that it consists substantially of a plurality of crystallites having additional mesoporosity the volume of which is in the range 0.09 to 0.25 cc/g as measured by nitrogen adsorption at 77° K and calculated by the BJH method.

The modified zeolite catalysts of the present invention are preferably those derived from zeolite ZSM-12 or zeolites of the TON structural type for example Theta-1, Nu-10, ZSM-22, KZ-2; ISI-1 with zeolites of the latter structure type being the more preferred. Further information on this latter structure type can be found in the Atlas of Zeolite Framework Types (C. Baerlocher, W. M. Meier, D. H., Olson, $5^{th}$ ed. Elsevier, Amsterdam, 2001) or the web-based version thereof. All the above-mentioned zeolites can be initially prepared by hydrothermal synthesis methods reported in the art. In a most preferred embodiment the zeolite is either Theta-1 or ZSM-22. The modified zeolite catalysts can also be derived from zeolites which have a two dimensional micropore structure but where the second channel in the zeolite is formed of 8-atom rings or smaller As mentioned above, the modified zeolite catalysts of the present invention are characterized by crystallites having significant mesoporosity which provide further access to the interior of the crystallites. This mesoporosity has pore volumes in the range 0.09 to 0.25 cc/g preferably 0.12 to 0.25 cc/g as measured by nitrogen adsorption at 77° K and calculated on the basis of an analysis of the isotherms so obtained using the Barrett-Joyner-Halenda (BJH) method. Details of this method can be found in J. Amer. Chem. Soc. (1951) 73 373-380.

Another general feature of the modified zeolite catalysts of the present invention which is apparent from electron microscopy is that they have a crystallite morphology which is relatively speaking dimensionally isotropic. In practical terms this means that the average ratio of the crystallite dimensions X and Y where X is the dimension along the axis parallel to the direction of the micropores and Y is the dimension along either of the other two axes perpendicular thereto is less than 4:1, preferably less than 3:1 and most preferably less than 2:1. This is to be contrasted with the crystallites of the original zeolite where the average ratio of X to Y is typically in excess of 5:1.

The modified zeolite catalysts of the present invention typically have a silicon to aluminium ratio of between 15:1 and 250:1, preferably between 30:1 and 200:1 and most preferably between 45:1 and 150:1.

Although the preferred catalytically active form of the modified zeolite catalyst is a hydrogen form, the modified zeolite catalyst of the present invention can in principle be wholly or partially converted into any other cationic form by conventional ion-exchange or impregnation techniques. Such forms can in principle include any stable metal cation but those of the Group IA and IIA metals, V, Cr, Mn, Fe, Co, Ni, Cu, Zn, Mo, W, Y Ti, Ga, the rare earths (e.g. Ce and La) and ammonium ion are preferred. Modified zeolite catalysts containing more than one cation can be created by sequential partial exchange or simultaneous exchange using a solution of more than one cation. The modified zeolite catalysts of the present invention can be prepared by a two step process. In the first step the zeolite made by hydrothermal synthesis is contacted with an alkaline solution having a pH at 25° C. in excess of 8 under conditions which will remove silicon from the structure, and possibly dissolve extraneous amorphous silica. Suitably this treatment is carried out by contacting the zeolite with an aqueous solution of one or more basic salts, for example the metal hydroxides, ammonium hydroxide, amines, phosphazenes, hydroxides of organic cations, pyridine, imidazole or quartemized amine hydroxides at a temperature in the range 20 to 250° C., preferably 30 to 150° C. and most preferably 40 to 90° C. Where preferably an aqueous hydroxide solution is used, the concentration of hydroxide in this aqueous solution is less than 10M, preferably less than 5M most preferably in the range 0.01 to 2M. Most preferably the hydroxides used are sodium hydroxide, potassium hydroxide, ammonium hydroxide, magnesium hydroxide, calcium hydroxide and tetramethyl-, tetraethyl-, tetrapropyl- and tetrabutylammonium hydroxide.

In an embodiment of the present invention the zeolite is converted into the hydrogen form prior to treatment with the aqueous alkaline solution. In another the alkaline treatment is performed on the hydrogen form of the zeolite which has been previously dealuminated to increase its silicon to aluminium ratio. For these materials the dealumination step may have been carried out by any of the techniques described in the art, such as acid treatment, hydrothermal treatment or combinations thereof.

After treatment with the aqueous alkaline solution the modified zeolite catalyst is in a second stage restored partially or completely to a catalytically active hydrogen form by known techniques such as ion-exchange with a solution of an ammonium salt followed by calcination under standard conditions. If desired, the modified zeolite catalyst can also be treated at the end of stage one and before stage two with a surface-modification agent such as a dicarboxylic acid, a bulky organic molecule (see for example U.S. Pat. Nos. 4,520,221 and 4,568,786), such as collidine, or bulky chelating/sequestering agents such as aminocarboxylates (e.g. EDTA, diethylenetriamine pentaacetic acid, hydroxyethylethylene diamine triacetate) and aminophosphates or aminophosphonates (e.g. aminotrimethylene phosphate, ethylenediamine tetramethylene phosphonate) or a hexahalosilicate salt. The purpose of this surface modification agent which in its active form consists of anions too large to penetrate the micropores of the modified zeolite catalyst, is to remove aluminium from the exterior of the crystallites. Additionally the exterior surface of the zeolite catalyst can be passivated by selective coking. In a preferred embodiment the modified zeolite catalyst is treated with oxalic acid or a hexafluorosilicate salt before use. If desired the modified zeolite catalyst can be formulated with a matrix of one or more additional metal oxides which are either amorphous or of low crystallinity. In such formulations the matrix may be selected from alumina, silica-alumina, silica, clays, the oxides of magnesium, titanium, boron, zirconium, vanadium, chromium, molybdenum, manganese, zinc, iron, nickel, cobalt, tungsten, antimony, ceria, lanthanum, and the other readily available rare earths as well as aluminium phosphates, zirconium phosphates, carbon, aluminates and combinations thereof. Preferably the matrix is comprised of the modified zeolite catalyst and at least one type of silica, silica/alumina or alumina, most preferably gamma-alumina. Binding agents typically used in the art can also additionally be employed.

The formulated modified zeolite catalyst can be formed into any shape useful for industrial-scale duty for example, extrudates, spheres, spray dried microspheres and the like.

Optionally, the modified zeolite catalyst may further comprise at least one other metal e.g. Ga, transition metals such as V, Cr, Mn, Group VIII metals, Cu, Zn, Mo, W, Y, Ti and the rare earths, preferably a Group VIII metal or combination of more than one of them. The incorporation of the Group VIII metal can be carried out by one or more steps of ion exchange, or by impregnation techniques such as the incipient wetness technique, all of them well known procedures described in the state of the art. Sources of the Group VIII metals include their corresponding nitrates, sulphates or halides.

According to the present invention the modified zeolite catalyst may comprise additionally at least one promoting element, selected from phosphorus, boron and their combinations. This promoting element is preferably phosphorus. These promoting elements can be incorporated into the catalyst by any of the well known procedures in the art. In the case of phosphorus, orthophosphoric acid, $H_3PO_4$, is most preferred.

Optionally the formulated modified zeolite catalyst described in the present invention can further comprise at least one halogen, preferable fluorine.

Typically a finished modified zeolite catalyst will conform to the following specification referred to the total weight:
  0.1 to 99 wt % of the modified zeolite catalyst;
  0.1 to 99 wt % of matrix;
  0 to 20% of a Group VIII metal.

In a preferred specification, the percentages will be:
  0.5 to 90% of the modified zeolite catalyst;
  0.1 to 75% of matrix;
  0 to 10% of a Group VIII metal.

In a most preferred specification, the percentages will be:
  1 to 80% of the modified zeolite catalyst;
  0.1 to 60% of matrix;
  0 to 5% of a Group VIII metal.

The formulated modified zeolite catalyst can optionally contain up to 30% preferably up to 20% of other promoters, binding agents and the like.

The modified zeolite catalysts of the present invention either alone or in formulated form are suitable for converting lower alkanes and alkenes into higher hydrocarbon fractions rich in components boiling in the gasoline and diesel fuel boiling range. They are also effective catalysts for converting lower alcohols and the ethers thereof e.g. methanol and dimethylether, into liquid hydrocarbons or light alkenes. In particular the modified zeolite catalysts of the present invention show improved resistance to deactivation and selectivity to higher hydrocarbons when used to oligomerize light olefins at elevated temperature and pressure.

The present invention will now be further described with reference to the following figures and examples.

FIG. 1: shows the propylene conversion obtained with the zeolite catalysts described in Examples 1-2, tested as described in Examples 6-7, compared with that of the zeolite precursor H-THETA-1 (Si/Al=50) tested as described in Example 5.

Figure 2:
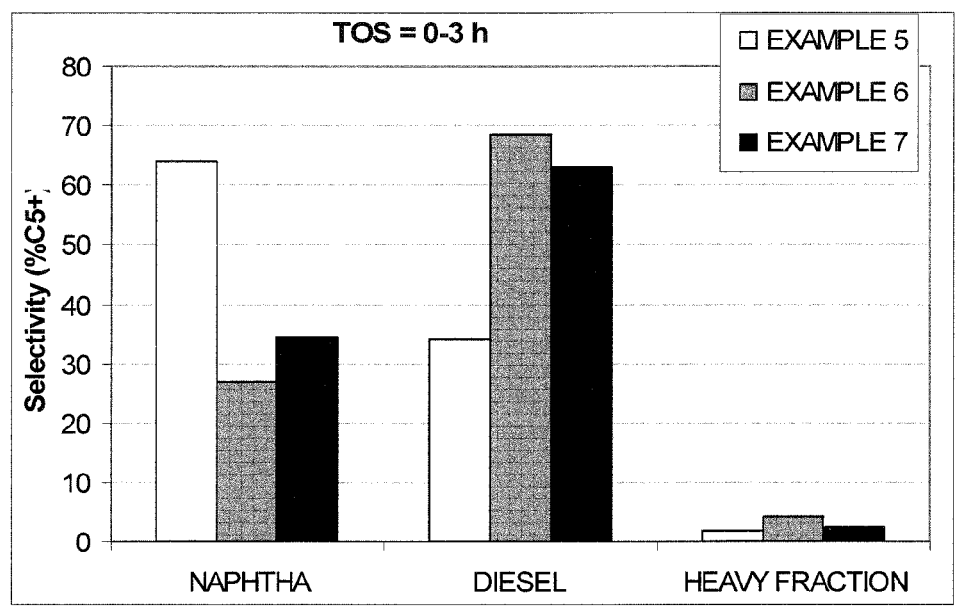

FIG. 2: shows the selectivity to different fractions in liquid products obtained with zeolites described in Examples 1-2, tested as described in Examples 6-7, compared with that of the zeolite precursor H-THETA-1 (Si/Al=50) tested as described in Example 5.

Figure 3:
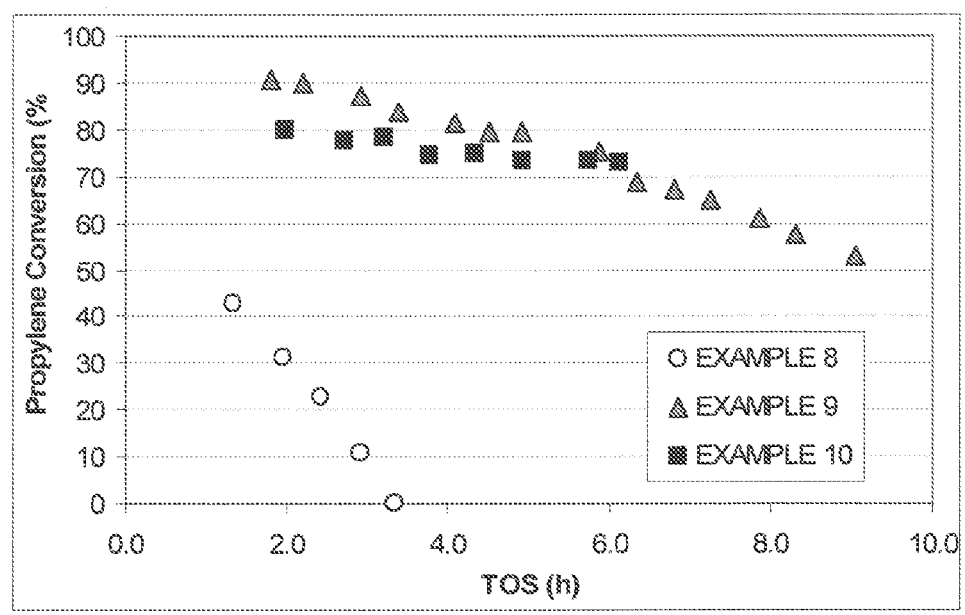

FIG. 3: shows the propylene conversion obtained with the zeolite catalysts described in Examples 3-4, tested as described in Examples 9-10, compared with that of the zeolite precursor H-THETA-1 (Si/Al=25) tested as described in Example 8.

Figure 4:
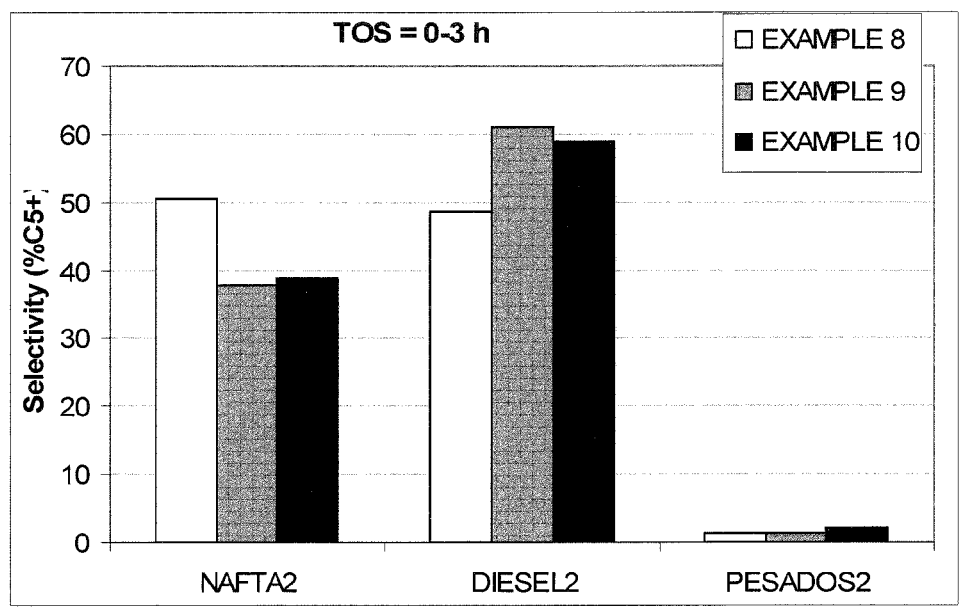

FIG. 4: shows the selectivity to different fractions in liquid products obtained with zeolite catalysts described in Examples 3-4, tested as described in Examples 9-10, compared with that of the zeolite precursor H-THETA-1 (Si/Al=25) tested as described in Example 8.

EXAMPLE 1

3 g of a THETA-1 zeolite in its hydrogen form (H-THETA-1, Si/Al=50) was suspended in 100 ml of a 0.2M sodium hydroxide aqueous solution and vigorously stirred for 30 min at 80° C. The reaction was then quenched by cooling down in an ice bath. The remaining solid was separated by filtration, washed with distillate water and dried overnight at 100° C. The alkaline treated THETA-1 was then converted to its acid form by three consecutive exchanges with a 0.1 M $NH_4NO_3$ solution at 83° C. for 2 hours and using a weight ratio of solution to solid of 20. Finally the sample is calcined for 5 hours at 450° C. Relative to the untreated zeolite the product of this process exhibited significant mesoporosity when studied by transmission electron microscopy and measured by nitrogen adsorption (77° K) and the BJH method ($V_{mesopore}$=0.107 cm$^3$g$^{-1}$).

EXAMPLE 2

3 g of a THETA-1 zeolite in its hydrogen form (H-THETA-1, Si/Al=50) was suspended in 100 ml of a 0.2M sodium hydroxide aqueous solution and vigorously stirred for 30 min at 85° C. Then the reaction was quenched by cooling down in an ice bath. The remaining solid was separated by filtration, washed with distillate water and dried overnight at 100° C. The alkaline treated THETA-1 was next suspended in a 2.0M aqueous solution of oxalic acid (solution/solid ratio of 10 wt/wt) and stirred for 2 hours at 70° C. The solid was separated by filtration, washed with distillate water and dried overnight at 100° C. Finally the sample was calcined for 3 hours at 375° C. Relative to the untreated zeolite the product of this process exhibited significant mesoporosity when studied by transmission electron microscopy and measured by nitrogen adsorption (77° K) and the BJH method ($V_{mesopore}$=0.117 cm$^3$g$^{-1}$).

EXAMPLE 3

Comparative 3 g of the THETA-1 zeolite used in Example 8 in its hydrogen form (H-THETA-1, Si/Al=25) was suspended in 100 ml of a 0.2M sodium hydroxide aqueous solution and vigorously stirred for 30 min at 85° C. The reaction was then quenched by cooling down in an ice bath. The remaining solid was separated by filtration, washed with distillate water and dried overnight at 100° C. The alkaline treated THETA-1 was next converted to its acid form by three consecutive exchanges with a 0.1 M NH$_4$NO$_3$ solution at 80° C. for 2 hours and using a weight ratio of solution to solid of 20. Finally the sample was calcined for 5 hours at 450° C. Relative to the untreated zeolite the product of this process showed lesser mesoporosity when studied by transmission electron microscopy and measured by nitrogen adsorption (77° K) and the BJH method ($V_{mesopore}$=0.067 cm$^3$g$^{-1}$). Although not according to the invention, this example shows that mesoporosity can be introduced into THETA-1 samples with little starting mesoporosity.

EXAMPLE 4

H-THETA-1 zeolite (Si/Al=25) was refluxed for 1 hour at room temperature in a 16.5 M Hydrochloric acid solution, using a solution/solid weight ratio of 67.3 g of the dealuminated THETA-1 zeolite was then suspended in 100 ml of a 1.0M sodium hydroxide aqueous solution and vigorously stirred for 30 min at 80° C. The reaction was then quenched by cooling down in an ice bath. The remaining solid was next separated by filtration, washed with distillate water and dried overnight at 100° C. The alkaline treated THETA-1 was then converted to its acid form by three consecutive exchanges with a 0.1 M NH$_4$NO$_3$ solution at 80° C. for 2 hours and using a weight ratio of solution to solid of 20. Finally the sample was calcined for 5 hours at 450° C. Relative to the untreated zeolite the product of this process exhibited significant mesoporosity when studied by transmission electron microscopy and measured by nitrogen adsorption (77° K) and the BJH method ($V_{mesopore}$=0.092 cm$^3$g$^{-1}$).

EXAMPLE 5

Comparative

THETA-1 zeolite in its hydrogen form (H-THETA-1, Si/Al=50) showing lesser mesoporosity by transmission electron microscopy ($V_{mesopore}$=0.084 cm$^3$g$^{-1}$) was pelletized, crushed and sieved to a particle size of 0.2-0.4 mm. 0.5 g of this pelletized sample were diluted with silicon carbide (0.64 mm-0.25 mm) to obtain a bed volume of 4.0 cm$^3$. The mixture was loaded into a down-flow stainless steel fixed bed reactor. A C3$^=$:C3 (propylene/propane) feedstock (60:40 wt:wt) was then fed to the reactor as a liquid by means of a Gilson piston pump. During the reaction, the pressure was controlled electronically through a Badger pneumatic valve. The temperature in the catalyst bed was controlled electronically by means of two independent heating zones with the corresponding thermocouples properly placed inside the catalytic bed. Oligomerization experiments were carried out at 200° C., 40 bar pressure and an alkene WHSV=6h$^{-1}$. Variation of propylene conversion with time on stream (TOS) is presented in FIG. 1. The selectivity to different fractions in the liquid product recovered at the outlet of the reactor during the first three hours TOS is enclosed in FIG. 2.

EXAMPLE 6

The alkaline treated zeolite prepared as described in Example 1 was pelletized, crushed and sieved to a particle size of 0.2-0.4 mm. 0.5 g of this pelletized sample were diluted with silicon carbide (0.64 mm-0.25 mm) to obtain a bed volume of 4.0 cm$^3$. The mixture was then loaded into a down-flow stainless steel fixed bed reactor, and a C3$^=$:C3 feedstock (60:40 wt:wt) processed as described in Example 5.

Variation of propylene conversion with time on stream (TOS) is compared with that of hydrogen form of the zeolite precursor in FIG. 1. It can be seen that not only is the initial activity greatly improved, but also the deactivation rate is decreased as compared to the hydrogen form. The selectivity to different fractions in the liquid product recovered at the outlet of the reactor during the first three hours TOS is shown in FIG. 2. This reveals that the selectivity to diesel in these experimental conditions is doubled as compared to the untreated zeolite.

EXAMPLE 7

The alkaline treated zeolite prepared as described in Example 2 was pelletized, crushed and sieved to a particle size of 0.2-0.4 mm. 0.5 g of this pelletized sample was diluted with silicon carbide (0.64 mm-0.25 mm) to obtain a bed volume of 4.0 cm$^3$. The mixture was then loaded into a down-flow stainless steel fixed bed reactor, and a C3$^=$:C3 feedstock (60:40 wt:wt) processed as described in Example 5.

Variation of propylene conversion with time on stream (TOS) is compared with that of the hydrogen form of the zeolite precursor in FIG. 1. It can be seen that the initial activity is increased to values close to 95% and, moreover, no deactivation is observed along the 8 hours TOS. The selectivity to different fractions in the liquid product recovered at the outlet of the reactor during the first three hours TOS is shown in FIG. 2. The selectivity to the desired diesel fraction is increased almost 30 points.

EXAMPLE 8

Comparative

An untreated THETA-1 zeolite sample in its hydrogen form (H-THETA-1, Si/Al=25) showing lesser mesoporosity ($V_{mesopore}$<0.060 cm$^3$g$^{-1}$) was pelletized, crushed and sieved to a particle size of 0.2-0.4 mm. 0.5 g of this pelletized sample were diluted with silicon carbide (0.64 mm-0.25 mm) to obtain a bed volume of 4.0 cm$^3$. The mixture was then loaded into a down-flow stainless steel fixed bed reactor, and a C3$^=$:C3 feedstock (60:40 wt:wt) processed as described in Example 5.

Variation of propylene conversion with time on stream (TOS) is compared with that other zeolite catalysts in FIG. 3. The selectivity to different fractions in the liquid product recovered at the outlet of the reactor during the first three hours TOS is shown in FIG. 4.

EXAMPLE 9

Comparative

The alkaline treated zeolite prepared as described in Example 3 was pelletized, crushed and sieved to a particle size of 0.2-0.4 mm. 0.5 g of this pelletized sample were diluted with silicon carbide (0.64 mm-0.25 mm) to obtain a bed volume of 4.0 cm$^3$. The mixture was then loaded into a down-flow stainless steel fixed bed reactor, and a C3$^=$:C3 feedstock (60:40 wt:wt) processed as described in Example 5.

Variation of propylene conversion with time on stream (TOS) is compared with that of the zeolite precursor in FIG. 3. It can be seen that not only is the initial activity greatly improved, but also the deactivation rate is decreased as compared to the hydrogen form of the zeolite precursor. The selectivity to different fractions in the liquid product recovered at the outlet of the reactor during the first three hours TOS is shown in FIG. 4.

EXAMPLE 10

The alkaline treated zeolite prepared as described in Example 4 was pelletized, crushed and sieved to a particle size of 0.2-0.4 mm. 0.5 g of this pelletized sample were diluted with silicon carbide (0.64 mm-0.25 mm) to obtain a bed volume of 4.0 cm$^3$. The mixture was then loaded into a down-flow stainless steel fixed bed reactor, and a C3$^=$:C3 feedstock (60:40 wt:wt) processed as described in Example 5.

Variation of propylene conversion with time on stream (TOS) is compared with that of the hydrogen form of the zeolite precursor in FIG. 3. It can be seen that not only is the initial activity greatly improved, but also the deactivation rate is decreased as compared to the hydrogen form. The selectivity to different fractions in the liquid product recovered at the outlet of the reactor during the first three hours TOS is shown in FIG. 4. There it is shown that the selectivity to diesel in these experimental conditions is considerably increased as compared to the hydrogen form of the untreated zeolite.

The invention claimed is:

1. A modified zeolite catalyst consisting essentially of a zeolite of a TON structural type which consists of a one-dimensional micropore structure of channels made from rings containing between 8 and 12 silicon/aluminium atoms wherein the zeolite has been modified to consist essentially of a plurality of crystallites having additional mesoporosity over the pore volume of an untreated zeolite, the volume of which is in the range 0.09 to 0.25 cc/g as measured by nitrogen adsorption at 77° K and calculated by the BJH method, and the modified zeolite catalyst has a silicon to aluminum ratio between 45:1 and 150:1.

2. A modified zeolite catalyst as claimed in claim 1 characterized in that the average ratio of the crystallite dimensions X and Y, where X is the dimension along the axis parallel to the direction of the micropores and Y is the dimension along either of the other two axes perpendicular thereto, is less than 3:1.

3. A modified zeolite catalyst as claimed in claim 2 characterized in that the average ratio of the crystallite dimensions X and Y, where X is the dimension along the axis parallel to the direction of the micropores and Y is the dimension along either of the other two axes perpendicular thereto, is less than 2:1.

4. A modified zeolite catalyst as claimed in claim 1 characterised in that it is in a form which contains one or more cations selected from the group comprising metal cations of the Group IA and IIA metals, V, Cr, Mn, Fe, Co, Ni, Cu, Zn, Mo, W, Y Ti, Ga, Ce and La and ammonium ion.

5. A modified zeolite catalyst as claimed in claim 1 characterised in that it has been treated with oxalic acid or a hexafluorosilicate salt.

6. A catalyst formulation comprising a modified zeolite catalyst as claimed in claim 1 and a metal oxide.

7. A catalyst formulation as claimed in claim 6 characterised in that the metal oxide is selected from silica, silica/alumina and alumina.

8. A process for preparing the modified zeolite catalyst of claim 1 comprising the steps of (1) treating a crystalline zeolite with an alkaline solution at a pH at 25° C. of greater than 8 under conditions which generate mesoporosity in the crystallites thereof and (2) converting the product of step (1) into a hydrogen form.

9. A process as claimed in claim 8 characterised in that the alkaline solution comprises aqueous sodium hydroxide or potassium hydroxide.

10. A modified zeolite catalyst as claimed in claim 1, wherein the zeolite has been treated with a surface modification agent to remove aluminum from the exterior of the crystallites.

11. A modified zeolite catalyst as claimed in claim 1, wherein the modified zeolite catalyst further comprises at least one promoting element selected from the group consisting of phosphorous, boron, and combinations thereof.

12. A process as claimed in claim 8, comprising performing the alkaline treatment on the hydrogen form of the zeolite which has been previously dealuminated in order to increase its silicon to aluminium ratio.

* * * * *